(12) United States Patent
Miller et al.

(10) Patent No.: US 10,588,835 B2
(45) Date of Patent: Mar. 17, 2020

(54) ORAL CARE PRODUCT AND METHODS OF USE AND MANUFACTURE THEREOF

(71) Applicant: Colgate-Palmolive Company, New York, NY (US)

(72) Inventors: Jeffrey Merl Miller, Jackson, NJ (US); Venda Porter Maloney, Piscataway, NJ (US); Donghui Wu, Bridgewater, NJ (US); Adam Pepperney, Easton, PA (US); Hongwei Shen, Holmdel, NJ (US); Vyoma Patel, Hillsborough, NJ (US); Chi-Yuan Cheng, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/848,072

(22) Filed: Dec. 20, 2017

(65) Prior Publication Data

US 2018/0177695 A1    Jun. 28, 2018

Related U.S. Application Data

(60) Provisional application No. 62/439,228, filed on Dec. 27, 2016.

(51) Int. Cl.

| | | |
|---|---|---|
| *A61K 8/34* | (2006.01) | |
| *A61K 8/27* | (2006.01) | |
| *A61K 8/36* | (2006.01) | |
| *A61Q 11/00* | (2006.01) | |
| *A61K 8/03* | (2006.01) | |
| *A61K 8/24* | (2006.01) | |
| *A61K 8/20* | (2006.01) | |
| *A61K 8/49* | (2006.01) | |
| *A61K 8/368* | (2006.01) | |
| *A61K 8/37* | (2006.01) | |
| *A61K 8/92* | (2006.01) | |

(52) U.S. Cl.
CPC .................. *A61K 8/34* (2013.01); *A61K 8/03* (2013.01); *A61K 8/20* (2013.01); *A61K 8/24* (2013.01); *A61K 8/27* (2013.01); *A61K 8/36* (2013.01); *A61K 8/368* (2013.01); *A61K 8/4926* (2013.01); *A61Q 11/00* (2013.01); *A61K 8/375* (2013.01); *A61K 8/4913* (2013.01); *A61K 8/92* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 3,535,421 A | 10/1970 | Briner et al. | |
| 3,678,154 A | 7/1972 | Widder et al. | |
| 3,696,191 A | 10/1972 | Weeks | |
| 3,991,177 A | 11/1976 | Vidra et al. | |
| 4,058,595 A | 11/1977 | Colodney | |
| 4,154,815 A | 5/1979 | Pader | |
| 4,355,022 A | 10/1982 | Rabussay | |
| 4,885,155 A | 12/1989 | Parran, Jr. et al. | |
| 4,992,420 A | 2/1991 | Neeser | |
| 5,000,939 A | 3/1991 | Dring et al. | |
| 6,723,305 B2 | 4/2004 | Depierro et al. | |
| 6,762,160 B2 * | 7/2004 | Barbeau | A61L 2/186 510/161 |
| 9,044,466 B2 | 6/2015 | Cohen et al. | |
| 9,622,962 B2 | 4/2017 | Lewus et al. | |
| 9,682,026 B2 | 6/2017 | Kohli et al. | |
| 9,724,278 B2 | 8/2017 | Lambert | |
| 2005/0281762 A1 * | 12/2005 | Modak | A61K 8/27 424/59 |
| 2015/0305993 A1 | 10/2015 | Rege et al. | |

FOREIGN PATENT DOCUMENTS

| | | | |
|---|---|---|---|
| EP | 0518798 | 12/1994 | |
| RU | 2483709 | 6/2013 | |
| WO | WO-2012064339 A1 * | 5/2012 | ............... A61K 8/03 |

OTHER PUBLICATIONS

Jia-Yuan Liu, Di Wu, Wei-Ming Sun, Ying Li and Zhi-Ru Li. Trivalent acid radical-centered YLi4+ (Y=PO4, AsO4, VO4) cations: new polynuclear species designed to enrich the superalkali family. Dalton Trans., 2014, 43, 18066 (Year: 2014).*

"Phosphoric Acid" in Wikipedia, downloaded Apr. 3, 2019 from https://en.wikipedia.org/wiki/Phosphoric_acid (Year: 2019).*

International Search Report and Written Opinion of the International Searching Authority in International Application No. PCT/US2017/067486, dated Mar. 9, 2018.

Triumph Pharmaceuticals, 2014, "Activated Mouthwash with 12 Hour Fresh Breath + Maximum Plague & Gingivitis Protection," Database Mintel GNPD AN: 2875229.

Triumph Pharmaceuticals, 2015, "Gum & Plague Activated Mouhtwash," Database Mintel GNPD AN: 3541527.

\* cited by examiner

*Primary Examiner* — Michael P Cohen

(57) ABSTRACT

This invention relates to a dual phase mouthwash comprising a hydrophilic phase, a hydrophobic phase, and a hydrotrope, wherein the hydrophilic phase comprises an effective amount of a preservative selected from potassium sorbate, sodium benzoate, benzyl alcohol, and a combination thereof, and CPC and a monovalent acid, as well as to methods of using and of making such compositions.

17 Claims, No Drawings

ORAL CARE PRODUCT AND METHODS OF USE AND MANUFACTURE THEREOF

CROSS-REFERENCE TO RELATED APPLICATIONS

This application claims priority to and the benefit of U.S. Provisional Application No. 62/439,228, filed on Dec. 27, 2016, the contents of which are hereby incorporated by reference in its entirety.

FIELD OF THE INVENTION

This invention relates to a preservative system for dual phase mouthwash composition comprising (i) a hydrophilic phase, (ii) a hydrophobic phase, (iii) a preservative selected from potassium sorbate, sodium benzoate, benzyl alcohol, and the combinations thereof, (iv) cetylpyridinium chloride (CPC), and (v) a monovalent acid (e.g., phosphoric acid and/or HCl), as well as to methods of using and of making these compositions.

BACKGROUND OF THE INVENTION

Because of their high-water content, mouthwashes are challenging to preserve. Previous patents or patent applications have postulated that the hydrophilic phases of dual phase mouthwashes prepared with CPC and sodium fluoride (NaF) are preserved by the presence of sodium benzoate, potassium sorbate and/or methylisothiazolinone (MIT). This invention finds that the removal of both a fluoride source and MIT from a mouthwash greatly compromises its preservation, and that the preservation is dependent on a number of factors, including: 1) the presence of CPC, 2) the presence of benzyl alcohol, 3) the nature of a flavor used in the mouthwash, 4) the type of acid used to adjust the pH of the mouthwash, with a monovalent acid (e.g., phosphoric acid and/or HCl) being preferred over a multivalent acid (e.g., citric acid), and 5) the interaction between preservatives and CPC.

BRIEF SUMMARY OF THE INVENTION

It is now surprisingly discovered that the dual phase mouthwashes comprising (i) a hydrophilic phase including a hydrotrope, (ii) a hydrophobic phase, (iii) a preservative selected from sodium benzoate, potassium sorbate, benzyl alcohol, and a combination thereof, (iv) CPC and (v) a monovalent acid (e.g., phosphoric acid), are stable and effective.

It is now also surprisingly discovered that the preservation of a dual phase mouthwash is dependent on a number of factors, including: 1) the presence of CPC, 2) the presence of benzyl alcohol, 3) the nature of a flavor used in the mouthwash, 4) the type of acid used to adjust the pH of the mouthwash, with a monovalent acid (e.g., phosphoric acid and/or HCl) being preferred over a multivalent acid (e.g., citric acid), and 5) the interaction between preservatives and CPC.

The invention thus encompasses oral care compositions and methods of using the same that are effective in inhibiting or reducing the accumulation of plaque, reducing levels of acid producing (cariogenic) bacteria, remineralizing teeth, and inhibiting or reducing gingivitis. The invention also encompasses compositions and methods to clean the oral cavity and provide improved methods of promoting oral health and/or systemic health, including cardiovascular health, e.g., by reducing potential for systemic infection via the oral tissues.

The invention thus provides a mouthwash composition (a Composition of the Invention), comprising (i) a hydrophilic phase including a hydrotrope, (ii) a hydrophobic phase, (iii) a preservative selected from sodium benzoate, potassium sorbate, benzyl alcohol, and a combination thereof, (iv) CPC, and (v) a monovalent acid (e.g., phosphoric acid and/or HCl).

The Compositions of the Invention may comprise additional ingredients, e.g., selected from one or more of water, surfactants, solvents, vitamins, minerals, polymers, enzymes, humectants, thickeners, additional antimicrobial agents, additional preservatives, flavorings, colorings and/or combinations thereof. In particular embodiments, the invention may comprise an anti-calculus agent, and/or may comprise a synthetic anionic polymeric polycarboxylate.

Effective amounts for the preservatives in the Compositions of the Invention, separately or in combination, are, for example, as follows, by weight: sodium benzoate less than 1%, e.g. about 0.01—about 0.5% or about 0.08-about 0.3%, e.g., about 0.1%; potassium sorbate less than 1%, e.g. about 0.01—about 0.5% or about 0.07—about 0.3%, e.g., about 0.1%; benzyl alcohol less than 1%, e.g., about 0.01-about 1% or about 0.08-about 0.8%, e.g., about 0.5% or about 0.3%.

The invention further encompasses methods comprising applying compositions effective upon application to the oral cavity, e.g., rinsing the oral cavity, optionally in conjunction with brushing, to (i) reduce or inhibit formation of dental caries, (ii) reduce or inhibit demineralization and promote remineralization of the teeth, (iii) reduce hypersensitivity of the teeth, (iv) reduce or inhibit gingivitis, (v) promote healing of sores or cuts in the mouth, (vi) reduce levels of acid producing bacteria, (vii) to increase relative levels of arginolytic bacteria, (viii) inhibit microbial biofilm formation in the oral cavity, (ix) raise and/or maintain plaque pH at levels of at least pH 5.5 following sugar challenge, (x) reduce plaque accumulation, (xii) treat, relieve or reduce dry mouth, (xii) clean the teeth and oral cavity (xiii) reduce erosion, (xiv) whiten teeth, (xv) immunize the teeth against cariogenic bacteria; and/or (xvi) promote systemic health, including cardiovascular health, e.g., by reducing potential for systemic infection via the oral tissues.

DETAILED DESCRIPTION OF THE INVENTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention thus provides, in a first embodiment, a dual phase mouthwash (Composition 1.0), comprising a hydrophilic phase; a hydrotrope; a hydrophobic phase; and an effective amount of a preservative selected from potassium sorbate, sodium benzoate, benzyl alcohol, and a combination thereof; CPC; and a monovalent acid.

For example, any of the following compositions:

1.0.1. Composition 1.0 wherein the wherein hydrophobic and hydrophilic phases spontaneously separate following mixing of the phases.
1.0.2. Any of the foregoing compositions wherein the monovalent acid is phosphoric acid and/or HCl.
1.0.3. Any of the foregoing compositions wherein the monovalent acid is phosphoric acid.
1.0.4. Any of the foregoing compositions wherein the hydrotrope component of the hydrophilic phase comprises a polyglycol, a polyhydric alcohol, or a mixture thereof.
1.0.5. Any of the foregoing compositions wherein the hydrotrope component comprises ethylene glycol, propylene glycol, glycerin, diethylene glycol, di-propylene glycol, tripropylene glycol, xylene glycol, 1,3-butylene glycol, 1,4-butylene glycol, 1,2,6-hexanetriol, sorbitol, xylitol, or a combination thereof.
1.0.6. Any of the foregoing compositions wherein the hydrotrope component comprises glycerin, propylene glycol, and/or 1,3 propanediol.
1.0.7. Any of the foregoing compositions wherein the hydrotrope component comprises glycerin.
1.0.8. Any of the foregoing compositions wherein the hydrotrope component comprises glycerin in an amount of, about 1 to about 40%, e.g., about 5 to about 25%, about 10% or about 15% or about 20%, by weight of the composition.
1.0.9. Any of the foregoing compositions wherein the hydrophobic phase comprises an oil selected from isopropyl myristate, mineral oil, an edible oil, and combinations thereof.
1.0.10. Any of the foregoing compositions comprising from 1% to 90% by volume of the hydrophilic phase.
1.0.11. Any of the foregoing compositions having a about 13:87 hydrophobic to hydrophilic weight ratio.
1.0.12. Any of the foregoing compositions wherein the hydrophilic phase comprises the hydrotrope component.
1.0.13. Any of the foregoing compositions wherein the preservatives are present, separately or in combination, in amounts by weight of the composition: sodium benzoate less than 1%, e.g. about 0.01—about 0.5% or about 0.08-about 0.3%, e.g., about 0.1%; potassium sorbate less than 1%, e.g. about 0.01—about 0.5% or about 0.07—about 0.3%, e.g., about 0.1%; benzyl alcohol less than 1%, e.g., about 0.01-about 1% or about 0.08-about 0.8%, e.g., about 0.5% or about 0.3% or about 0.1%.
1.0.14. Any of the foregoing compositions wherein the preservatives are present, separately or in combination, in amounts by weight of the composition: potassium sorbate 0.01-0.5%; sodium benzoate 0.01-0.5%; benzyl alcohol 0.01-1%.
1.0.15. Any of the foregoing composition wherein the preservatives are present, separately or in combination, in amounts by weight of the composition: (i) about 0.08%-about 0.3% sodium benzoate, (ii) about 0.07%-about 0.3% potassium sorbate and/or about 0.08%—about 0.8% benzyl alcohol.
1.0.16. Any of the foregoing compositions wherein the hydrophilic phase further comprises CPC, e.g., in an amount of about 0.001-1% or about 0.01—about 0.1%, e.g., about 0.075% by weight of the composition.
1.0.17. Any of the foregoing compositions wherein the hydrophilic phase further comprises phosphoric acid at a concentration of from about 0.01 to about 5% or about 0.05 to about 2%, e.g., 0.08%, by weight of the composition.
1.0.18. Any of the foregoing composition comprising one or more of flavors selected from spearmint, peppermint, wintergreen, sassafras, clove, sage, eucalyptus, marjoram, cinnamon, lemon, lime, grapefruit, orange, menthol, carvone, anethole, optacool, and a combination thereof.
1.0.19. Any of the foregoing composition comprising one or more of flavors selected from spearmint, peppermint, wintergreen, menthol, optacool and a combination thereof.
1.0.20. Any of the foregoing composition comprising one or more of flavors in an amount of about 0.01—about 2% by weight of the composition.
1.0.21. Any of the foregoing compositions further comprising an anti-calculus agent for example polyphosphate, e.g., pyrophosphate, tripolyphosphate, or hexametaphosphate, e.g., in salt form, e.g., sodium or potassium salt form, e.g., in an amount of from 0.1-3%.
1.0.22. The foregoing composition wherein the anti-calculus agent is a pyrophosphate selected from tetrasodium pyrophosphate and tetrapotassium pyrophosphate and mixtures thereof.
1.0.23. The foregoing composition comprising 0.1 to 1% tetrasodium pyrophosphate and 1-2% tetrapotassium pyrophosphate, e.g. 0.25-0.75% tetrasodium pyrophosphate and 1.0-1.5% tetrapotassium pyrophosphate.
1.0.24. Any of the preceding compositions comprising at least one polymer selected from polyethylene glycols; synthetic anionic polymeric polycarboxylate, such as polyvinylmethyl ether maleic acid copolymers; polysaccharides (e.g., cellulose derivatives, for example carboxymethyl cellulose or polysaccharide gums, for example xanthan gum or carrageenan gum); and combinations thereof.
1.0.25. Any of the foregoing compositions comprising a synthetic anionic polymeric polycarboxylate, e.g., in an amount of 1-10%, e.g., 2.5-7.5%.
1.0.26. The foregoing composition wherein the synthetic anionic polymeric polycarboxylate is a 1:4 to 4:1 copolymer of maleic anhydride or acid with another polymerizable ethylenically unsaturated monomer, e.g. methyl vinyl ether/maleic anhydride having a molecular weight (M.W.) of 30,000 to 5,000,000 daltons, for example 1000 kD-3000 kD.
1.0.27. The foregoing composition comprising a co-polymer of methyl vinyl ether/maleic anhydride having the general structure $\{CH_2—CH(OCH_3)—CH(COOH)—CH(COOH)\}_n$, viscosity of CP at 25° C. of 1-3 kCP, e.g., $1.7 \times 10^3$ CP, and nominal molecular weight of 1000 kD —3000 kD, e.g., $1.98 \times 10^6$, for example in an amount by weight of 1-10%, e.g., 5%
1.0.28. Any of the foregoing compositions which is ethanol-free.
1.0.29. Any of the foregoing compositions further comprising a basic amino acid in free or salt for, for example arginine, for example in an amount of 0.1-3%, e.g. 0.8%,
1.0.30. Any of the foregoing compositions further comprising a soluble calcium salt, e.g., selected from calcium glycerophosphate and salts of soluble carboxylic acids, and mixtures thereof, e.g., wherein the calcium salt is selected from calcium citrate, calcium malate, calcium lactate, calcium formate, calcium fumarate, calcium gluconate, calcium lactate gluconate, calcium aspartate, and calcium propionate, and mixtures thereof.

1.0.31. Any of the foregoing compositions wherein the pH is between 4 and 6.5, e.g. 4.5.
1.0.32. Any of the foregoing compositions further comprising an abrasive or particulate.
1.0.33. Any of the foregoing compositions comprising a nonionic surfactant, e.g., in an amount of from 0.5 -5%, for example 1-2%, selected from polaxamers (e.g., polaxamer 407), polysorbates (e.g., polysorbate 20), polyoxyl hydrogenated castor oil (e.g., polyoxyl 40 hydrogenated castor oil), and mixtures thereof.
1.0.34. Any of the foregoing compositions comprising at least one humectant.
1.0.35. Any of the foregoing compositions comprising at least one humectant selected from glycerin, sorbitol, propylene glycol, and combinations thereof, e.g., in a total amount of about 5-about 40%, e.g., about 10—about 25%, e.g., about 20%, about 15, or about 10%.
1.0.36. Any of the foregoing compositions 1.0.34 and 1.0.35 wherein the at least one humectant is sorbitol.
1.0.37. The foregoing composition wherein sorbitol is present in an amount of: about 1 to about 30%, e.g., about 3 to about 15%, e.g., about 5% or about 10%, by weight of the composition.
1.0.38. Any of the foregoing compositions comprising polymer films.
1.0.39. Any of the foregoing compositions comprising fragrance and/or coloring.
1.0.40. Any of the foregoing compositions comprising at least 50% water.
1.0.41. Any of the foregoing compositions comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., CPC, benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, other metal ions (e.g., zinc salts, for example zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidine derivatives, nicin preparations, chlorite salts; and mixtures of any of the foregoing.
1.0.42. Any of the foregoing compositions comprising an antioxidant, e.g., selected from the group consisting of Co-enzyme Q10, PQQ, Vitamin C, Vitamin E, Vitamin A, anethole-dithiothione, and mixtures thereof.
1.0.43. Any of the foregoing compositions comprising a whitening agent.
1.0.44. Any of the foregoing compositions comprising a whitening agent selected from a whitening active selected from the group consisting of peroxides, metal chlorites, perborates, percarbonates, peroxyacids, hypochlorites, and combinations thereof.
1.0.45. Any of the foregoing compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.
1.0.46. Any of the foregoing compositions further comprising an agent that interferes with or prevents bacterial attachment, e.g., solbrol or chitosan.
1.0.47. Any of the foregoing compositions further comprising a physiologically acceptable potassium salt, e.g., potassium nitrate or potassium chloride, in an amount effective to reduce dentinal sensitivity.
1.0.48. Any of the foregoing compositions comprising from 0.01% to 1% of a physiologically acceptable potassium salt, e.g., potassium nitrate and/or potassium chloride.
1.0.49. Any of the foregoing compositions, wherein the composition comprises a hydrophilic phase, a hydrotrope, hydrophobic and, wherein the composition further comprises:
i.) about 0.1% potassium sorbate by weight of the composition,
ii.) about 0.1% sodium benzoate by weight of the composition,
iii.) about 0.5% benzyl alcohol by weight of the composition,
iv.) CPC, and
v.) phosphoric acid.
1.0.50. Any of the foregoing compositions, wherein the composition comprises a hydrophilic phase, a hydrotrope, hydrophobic and, wherein the composition further comprises:
i.) about 0.1% potassium sorbate by weight of the composition,
ii.) about 0.1% sodium benzoate by weight of the composition,
iii.) about 0.5% benzyl alcohol by weight of the composition, and
iv.) about 0.075% CPC by weight of the composition, and
v.) phosphoric acid.
1.0.51. Any of the foregoing compositions, wherein the composition comprises a hydrophilic phase, a hydrotrope, hydrophobic and, wherein the composition further comprises:
i.) about 0.1% potassium sorbate by weight of the composition,
ii.) about 0.1% sodium benzoate by weight of the composition,
iii.) about 0.5% benzyl alcohol by weight of the composition,
iv.) about 0.075% CPC by weight of the composition, and
v.) about 0.08% phosphoric acid by weight of the composition.
1.0.52. Any of the foregoing compositions, wherein the composition comprises a hydrophilic phase, a hydrotrope, hydrophobic and, wherein the composition further comprises:
i.) about 0.1% potassium sorbate by weight of the composition,
ii.) about 0.1% sodium benzoate by weight of the composition,
iii.) about 0.5% benzyl alcohol by weight of the composition,
iv.) about 0.075% CPC by weight of the composition,
v.) about 0.08% phosphoric acid by weight of the composition, and vi.) about 0.01-2% one or more flavors by weight of the composition.

1.0.53. Any of the foregoing compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.0.54. Any of the foregoing composition is free of sodium fluoride.

1.0.55. Any of the foregoing composition is free of methylisothiazolinone.

1.0.56. Any of the preceding compositions further comprising a fluoride source other tan sodium fluoride, e.g., a fluoride salt, e.g., stannous fluoride, amine fluoride or wherein the fluoride is covalently bound to another atom, e.g., a monofluorophosphate, for example sodium monofluorophosphate, a fluorosilicate, e.g., sodium fluorosilicate or ammonium fluorosilicate, or a fluorosulfate, e.g., hexafluorosulfate, amine fluoride and combinations thereof.

1.0.57. A composition obtained or obtainable by combining the ingredients as set forth in any of the foregoing compositions.

Levels of active ingredients will vary based on the nature of the delivery system and the particular active. For example, the zinc salt may be present at levels from, e.g., about 0.05 to about 2 wt %, e.g., about 0.1 to about 1 wt %. Levels of additional antibacterial will vary similarly, depending on the agent used. For example, a triclosan mouthrinse may contain, e.g., about 0.03 wt % triclosan.

In another embodiment, the invention encompasses a method to improve oral health comprising applying an effective amount of the oral composition of any of the embodiments set forth above to the oral cavity of a subject in need thereof, e.g., a method to i. reduce or inhibit formation of dental caries,
ii. reduce, repair or inhibit early enamel lesions, e.g., as detected by quantitative light-induced fluorescence (QLF) or electrical caries measurement (ECM),
iii. reduce or inhibit demineralization and promote remineralization of the teeth,
iv. reduce hypersensitivity of the teeth,
v. reduce or inhibit gingivitis,
vi. promote healing of sores or cuts in the mouth,
vii. inhibit microbial biofilm formation in the oral cavity,
viii. raise and/or maintain plaque pH at levels of at least pH 5.5 following sugar challenge,
ix. reduce plaque accumulation,
x. treat dry mouth,
xi. enhance systemic health, including cardiovascular health, e.g., by reducing potential for systemic infection via the oral tissues,
xii. whiten teeth,
xiii. reduce erosion of the teeth,
xiv. immunize (or protect) the teeth against cariogenic bacteria and their effects, and/or
xv. clean the teeth and oral cavity.

The invention further comprises the use of any of sodium benzoate, potassium sorbate, benzyl alcohol, and combinations thereof in the manufacture of a Composition of the Invention, e.g., for use in any of the indications set forth in the above method.

The compositions of the present invention comprise a hydrophilic and a hydrophobic phase, and a hydrotrope component which when mixed form a temporary oil-in-water emulsion, which breaks down and separates back into the hydrophobic and hydrophilic phases within 5 seconds to one hour following mixing. Without intending to be bound by theory, it is believed that the high HLB of the hydrophobic phase allows for the complete separation of the two phases.

The hydrophobic phase of the composition of the present invention may contain any orally acceptable hydrophobic liquid, e.g., generally recognized as safe. Such materials are known in the art, and may include isopropyl myristate, liquid paraffin (mineral oil), edible oils such as olive oil, corn oil, coconut oil, soybean oil, and combinations thereof A preferred hydrophobic phase comprises liquid paraffin, isopropyl myristate. Preferably, the hydrophobic phase has a HLB of from 7 to 12, e.g., 10.

The hydrophilic phase of the compositions of the present invention are aqueous based, e.g., having from 40% to 95% by weight water. Other useful materials may also include orally acceptable alcohols, humectants, buffer agents or polymers. A humectant on a pure humectant basis, generally includes about 5% to about 50% in one embodiment or about 10% to about 25% in another embodiment by weight of the mouth wash composition. The hydrophilic phase may optionally include one or more polymers, e.g., in the hydrophilic phase, such as polyvinylmethyl ether maleic acid copolymers, polysaccharides (e.g. cellulose derivatives, for example carboxymethyl cellulose, or polysaccharide gums, for example xanthan gum or carrageenan gum). The compositions of the present invention may contain an orally acceptable polyvinylmethylether/maleic anhydride (PVME/MA) copolymer. The PVME/MA copolymer is present from 0.1% to 20%, for example 0.5% to 10% by weight. Generally the methyl vinyl ether to maleic anhydride ratio in the copolymer is 1:4 to 4:1, and the copolymer has an average molecular weight of 30,000 to 1,000,000, for example 30,000 to 500,000. Preferred PVME/MA copolymers include those under the GANTREZ brand from ISP (Wayne, N.J.). The PVME/MA copolymer may also act as an antibacterial enhancing agent if present in an antibacterial enhancing effective amount.

Preferably, the composition further comprises an aqueous buffer system. The buffer system may comprise at least one of an organic acid or an alkali metal salt thereof. The buffer system may comprise citric acid. Preferably, the buffer system may comprise phosphoric acid present at a concentration of from about 0.01 to about 5% or about 0.05 to about 2%, by weight of the composition. In some embodiments, phosphoric acid is present at a concentration of about 0.08%, by weight of the composition.

The mouthwash may comprise an anti-bacterial agent. A suitable anti-bacterial agent includes phenolic compounds, subject to determination of oral acceptability, those identified as having anti-inflammatory activity by Dewhirst (1980), Prostaglandins 20(2). 209-222, but are not limited thereto. Examples of antibacterial phenolic compounds include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexylresorcinol, 8-hydroxyquinoline and salts thereof, salicylic acid esters including menthyl salicylate, methyl salicylate and phenyl salicylate, phenol, pyrocatechol, salicylanilide, and thymol. Illustratively the total concentration of the at least one phenolic compound in a mouthwash of the present invention can be about 0.01% to about 5%, for example about 0.1% to about 2%, about 0.2% to about 1% or about 0.25% to about 0.5%.

Other suitable antibacterial agents include, without limitation, copper (II) compounds such as copper (II) chloride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as CPC (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. A further illustrative list of useful antibacterial agents is provided in U.S. Pat. No. 5,776,435 to Gaffar et al., incorporated herein by reference. If present, these antimicrobial agents are present in an antimicrobial effective total amount, typically about 0.001% to about 10%, for example about 0.1% to about 3% by weight, of the composition.

In some embodiments, the oral composition comprises CPC, in amounts of about 0.001-1%, e.g., about 0.01—about 0.5%, or about 0.01-about 0.1%, e.g., about 0.075%, by weight of the composition.

The composition of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint, spearmint, menthol, optacool, and/or wintergreen.

The flavoring agent is incorporated in the oral composition at a concentration of about 0.01 to about 2% or about 0.05 to about 1.5%, e.g., about 0.1%, about 0.6%, 0.025%, or about 0.02%, by weight of the composition.

It is surprisingly discovered that the preservation of the dual phase mouthwash composition is dependent on a number of factors, including: 1) the presence of CPC, 2) the presence of benzyl alcohol, 3) the nature of a flavor used in the composition, 4) the type of acid used to adjust the pH of the composition, a monovalent acid (e.g., phosphoric acid and/or HCl) being preferred over a multivalent acid (e.g., citric acid), and 5) the interaction between preservatives and CPC. Thus, in one embodiment, composition comprise a hydrophilic phase including a hydrotrope; a hydrophobic phase; an effective amount of a preservative selected from potassium sorbate, sodium benzoate, benzyl alcohol, and a combination thereof; CPC; and a monovalent acid (e.g., phosphoric acid and/or HCl). In another embodiment, composition comprise a hydrophilic phase including a hydrotrope; a hydrophobic phase; an effective amount of a preservative selected from potassium sorbate, sodium benzoate, benzyl alcohol, and a combination thereof; CPC; and phosphoric acid. Also in another embodiment, the composition includes a hydrotrope; a hydrophobic phase; an effective amount of a preservative selected from potassium sorbate, sodium benzoate, benzyl alcohol, and a combination thereof; CPC; and phosphoric acid, and wherein the composition is free of a fluoride source and MIT. Still in another embodiment, the composition comprises a hydrophilic phase including a hydrotrope; a hydrophobic phase; an effective amount of a preservative selected from potassium sorbate, sodium benzoate, benzyl alcohol, and a combination thereof; CPC; a flavor; and phosphoric acid. In another embodiment, the composition comprises a hydrophilic phase including a hydrotrope; a hydrophobic phase; an effective amount of a preservative selected from potassium sorbate, sodium benzoate, benzyl alcohol, and a combination thereof; CPC; a flavor; and phosphoric acid, and wherein the composition is free of a fluoride source and MIT. In a particular embodiment, the composition comprises a hydrophilic phase, a hydrophobic phase, a hydrotrope, about 0.1% potassium sorbate, about 0.1% sodium benzoate, and 0.5% benzyl alcohol, about 0.075% CPC, one or more flavors, and about 0.08% phosphoric acid.

Hydrotropes are known in the art, and include compounds that solubilizes hydrophobic compounds in aqueous solutions. Hydrotropes are low molecular weight amphiphilic compounds which resemble surfactants in as much as they have hydrophilic groups, and, in surfactant terms, what may be described as a low molecular weight hydrophobe. The hydrophilic group is may be attached to an organic moiety that is too short a group to confer true surface active properties. Hydrotropes useful in the present invention may include aromatic sulfonates, aromatic phosphate esters, di and polycarboxylates, polyglycols, and alcohols, including polyhydric alcohols. Hydrotropes useful in the present invention have a HLB value of from 7 to 18. Although any hydrotrope may be useful in the present invention (preferably GRAS), the hydrotrope may have a HLB value similar to that of the hydrophobic phase, and thus, the exact hydrotrope useful in the compositions will be dependent upon the composition of the hydrophobic phase. Preferably, the HLB of the coupling system is greater than the HLB of the hydrophobic phase, e.g., 10%, 15%, 20%, or 30% greater than the FMB of the hydrophobic phase. Methods of determining HLB is well known to those of skill in the art. The hydrotrope component in the present invention comprises one or more polyglycols and/or polyhydric alcohols, preferably a diol and/or a triol. Preferably, the coupling system comprises glycerine and propylene glycol. The exact ratio of glycerine and propylene glycol in the coupling system will depend on the desired HLB of the hydrotrope component of the present invention. As the hydrotrope lacks surfactant properties, the dispersion of the oil phase in the water is not thermodynamically stable, and an emulsion formed by mixing the two phases reverts back into separate and distinct phases immediately following mixing. Glycerin is used in certain embodiments as the hydrotrope component of the compositions herein. In some embodiments, glycerin is used as the hydrotrope component of the compositions herein, in an amount of, about 1 to about 40%, e.g., about 5 to about 25%, e.g., about 10% or about 15% or about 20%, by weight of the composition.

The compositions of the present invention incorporate one or more surfactants which are known in the art. Suitable surfactants include those which are reasonably stable throughout a wide pH range, for example, anionic, cationic, nonionic or zwitterionic surfactants. Preferred surfactants are nonionic surfactants. Preferably, the amount of surfactant in the compositions of the present invention is reduced to minimize the dispersion of the hydrophobic phase in the hydrophilic phase in the creation of emulsions which do not separate within 2 minutes from mixing the phases. It has been found that minimizing the surfactant content and the presence of hydrotropes allows for efficient separation of the two phases. In one embodiment of the present invention, the oral compositions are free, or substantially free of surfactants, especially anionic, cationic, and zwitterionic surfactants. Nonionic surfactants may be use in limited quantities in the present invention. Such nonionic surfactants may be defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. The compositions of the present invention may contain from 0.0001% to 0.01% by weight of a surfactant.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Chelating and Anti-calculus Agents

The oral care compositions of the invention also may optionally include one or more chelating agents able to complex calcium found in the cell walls of the bacteria. Binding of this calcium weakens the bacterial cell wall and augments bacterial lysis.

One group of agents suitable for use as chelating or anti-plaque agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.5 wt. % pyrophosphate ions, 0.9-3 wt. %.

These compounds also contribute to preservation of the compositions by lowering water activity.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water

Water is present in the oral compositions of the invention. Water, employed in the preparation of commercial oral compositions should be deionized and free of organic impurities. Water commonly makes up the balance of the compositions and includes 10% to 90%, e.g., 40% to 70% by weight of the oral compositions. This amount of water includes the free water which is added plus that amount which is introduced with other materials such as with sorbitol or any components of the invention.

Humecants

Within certain embodiments of the oral compositions, it is also desirable to incorporate a humectant to reduce evaporation and also contribute towards preservation by lowering water activity. Certain humectants can also impart desirable sweetness or flavor to compositions. The humectant, on a pure humectant basis, generally includes about 5% to about 70% or about 10% to about 65% or about 10% to about 40%, or about 15% to about 40% or about 30% to about 65% by weight of the composition, e.g., about 10%, about 15% or about 20%.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein. In one embodiment, sorbitol is used as the humectant component of the compositions herein, in an amount of, about 1 to about 30%, e.g., about 3 to about 15%, e.g., about 3%, about 5%, about 6.5% or about 10%, by weight of the composition.

Fluoride Ion Source:

The oral care compositions may further include one or more fluoride ion sources other than sodium fluoride, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium monofluorophosphate as well as mixtures thereof. Where the formulation may comprise calcium salts, the fluoride salts are preferably salts wherein the fluoride is covalently bound to another atom, e.g., as in sodium monofluorophosphate, rather than merely ionically bound, e.g., as in sodium fluoride.

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Enhancing oral health also provides benefits in systemic health, as the oral tissues can be gateways for systemic infections. Good oral health is associated with systemic health, including cardiovascular health. The compositions and methods of the invention are thus useful to enhance systemic health, including cardiovascular health.

EXAMPLES

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

To optimize the preservative system, the dependency of the preservation of the dual phase mouthwashes on a number of factors is studied. Those factors include 1) the presence of CPC, 2) the presence of benzyl alcohol, 3) the nature of the flavor, 4) the type of acid used to adjust the pH of the mouthwash, with phosphoric acid being preferred over citric acid, and 5) the interaction between preservatives and CPC.

An antimicrobial effectiveness test (AET) is used to determine the antimicrobial preservation effectiveness of water-based product formulations. Two types of AET tests are used to evaluate the preservation effectiveness, both of which are run for 28 days, and need to be passed for a formula to be considered preserved.

The first test (AET1) is a double inoculum challenge test run against an organism from the genus *Burkholderia*, which is known to be challenging to preserve mouthwash formulations against. This AET is used as a screening tool to evaluate the relative effectiveness of various formulas and is run on fresh samples. Acceptance criteria are more stringent than USP 39 <51> criteria for oral preparations.

The second (AET2) is a double inoculum challenge of bacteria, yeast, and mold including those prescribed by USP 39 <51> and using similar methodology and more stringent acceptance criteria as USP 39 <51. This testis run against samples aged 13 weeks at 40° C./75% RH.

Example 1

Factors Impacting Preservation of Oral Compositions

AET 1 using *Burkholderia* is utilized to test MIT, NaF, a preservative and a flavor's impact on the preservation of oral care compositions. Results of the comparative testing on Formulas 1-6 are shown in Table 1. The results of the comparative testing on Formulas 1-5 demonstrate that simply removal of MIT and NaF from the formulas may reduce preservation, while the results of the testing on Formula 6 demonstrate that the preservation of the oral composition is flavor dependent, and the increased amounts of potassium sorbate and sodium benzoate in the presence of CPC may compensate the reduced preservative efficacy caused by the removal of MIT and NaF.

TABLE 1

| Formula No. | CPC (%) | NaF (%) | MIT (ppm) | Potassium Sorbate/Sodium Benzoate/ Benzyl Alcohol | Flavor | Acid | pH | Meets acceptance criteria/Does not meet acceptance criteria |
|---|---|---|---|---|---|---|---|---|
| Formula 1 | 0.05 | 0.05 | 50 | 0.05/0/0 | Peppermint | Citric | 5.0 | Meet |
| Formula 1 | 0.05 | 0.05 | 50 | 0.05/0/0 | Spearmint | Citric | 5.0 | Meet |
| Formula 2 | 0.075 | 0.05 | 0 | 0.1/0/0 | Peppermint | Citric | 4.7 | Meet |
| Formula 3 | 0.075 | 0 | 50 | 0.05/0/0 | Peppermint | Cittic | 5.0 | Meet |
| Formula 3 | 0.075 | 0 | 50 | 0.05/0/0 | Spearmint | Citric | 5.0 | Meet |
| Formula 4 | 0.075 | 0 | 0 | 0.1/0/0 | Peppermint | Citric | 4.7 | Not meet |
| Formula 4 | 0.075 | 0 | 0 | 0.1/0/0 | Spearmint | Citric | 4.7 | Not meet |
| Formula 5 | 0.075 | 0 | 0 | 0.1/0/0 | Wintergreen | Citric | 4.2 | Not meet |
| Formula 6 | 0.075 | 0 | 0 | 0.1/0.1/0 | Peppermint | Citric | 4.5 | Meet |
| Formula 6 | 0.075 | 0 | 0 | 0.1/0.1/0 | Spearmint | Citric | 4.5 | Not meet |
| Formula 6 | 0.075 | 0 | 0 | 0.1/0.1/0 | Wintergreen | Citric | 4.5 | Not meet |

Formulas 1-6 are prepared with the following ingredients, weight percentages given with respect to the final dual phase formulation:

TABLE 2

| Ingredients | Formula 1 | | Formula 2 | Formula 3 | | Formula 4 |
|---|---|---|---|---|---|---|
| | Peppermint | Spearmint | Peppermint | Peppermint | Spearmint | Peppermint |
| Water | Balance | Balance | Balance | Balance | Balance | Balance |
| Mineral Oil - Heavy | 12.00 | 12.00 | 11.80 | 12.00 | 12.00 | 11.80 |
| Glycerin | 7.50 | 7.50 | 7.50 | 7.50 | 7.50 | 7.50 |

TABLE 2-continued

|  | Formula 1 | | Formula 2 | Formula 3 | | Formula 4 |
|---|---|---|---|---|---|---|
| Ingredients | Peppermint | Spearmint | Peppermint | Peppermint | Spearmint | Peppermint |
| Sorbitol |  |  | 5.50 |  |  | 5.50 |
| Peppermint Flavor | 1.10 |  | 1.20 | 1.10 |  | 1.20 |
| Spearmint Flavor |  | 0.75 |  |  | 0.75 |  |
| Wintergreen Flavor |  |  |  |  |  |  |
| Sodium Saccharin | 0.08 | 0.12 | 0.12 | 0.08 | 0.12 | 0.12 |
| Sucralose |  |  | 0.02 |  | 0.02 | 0.02 |
| Sodium Fluoride | 0.05 | 0.05 | 0.05 |  |  |  |
| CPC | 0.05 | 0.05 | 0.075 | 0.075 | 0.075 | 0.075 |
| Methylisothiazolinone | 0.05 | 0.05 |  | 0.05 | 0.05 |  |
| Potassium Sorbate | 0.05 | 0.05 | 0.10 | 0.05 | 0.05 | 0.10 |
| Sodium Dihydrogen Phosphate Monohydrate | 0.025 | 0.025 |  | 0.025 | 0.025 |  |
| Polysorbate 20 | 0.020 | 0.02 |  | 0.02 | 0.02 |  |
| Sucralose |  | 0.02 |  |  |  |  |
| Citric Acid | 0.010 | 0.01 | 0.05 | 0.01 | 0.01 | 0.05 |
| Silicone Antifoam |  |  | 0.005 |  |  | 0.005 |
| Color agents | 0.0005 | 0.0012 | 0.0008 | 0.0005 | 0.0012 | 0.0008 |
| Total | 100 | 100 | 100 | 100 | 100 | 100 |

TABLE 3

|  | Formula 4 | Formula 5 | Formula 6 | | |
|---|---|---|---|---|---|
| Ingredients | Spearmint | Wintergreen | Peppermint | Spearmint | Wintergreen |
| Water | Balance | Balance | Balance | Balance | Balance |
| Mineral Oil - Heavy | 12.17 | 12.25 | 12.20 | 12.50 | 12.50 |
| Glycerin | 7.50 | 7.50 | 10.00 | 10.00 | 10.00 |
| Sorbitol | 5.50 | 5.50 | 10.00 | 10.00 | 10.00 |
| Peppermint Flavor |  |  | 0.80 |  |  |
| Spearmint Flavor | 0.83 |  |  | 0.50 |  |
| Wintergreen Flavor |  | 0.75 |  |  | 0.50 |
| Sodium Saccharin | 0.12 | 0.12 | 0.12 | 0.12 | 0.12 |
| Sucralose | 0.02 | 0.02 | 0.02 | 0.02 | 0.02 |
| CPC | 0.075 | 0.075 | 0.075 | 0.075 | 0.075 |
| Potassium Sorbate | 0.10 | 0.10 | 0.10 | 0.10 | 0.10 |
| Sodium Benzoate |  |  | 0.1000 | 0.10 | 0.10 |
| Citric Acid | 0.05 | 0.075 | 0.085 | 0.085 | 0.085 |
| Silicone Antifoam | 0.005 | 0.005 | 0.005 | 0.005 | 0.005 |
| Color agents | 0.0013 | 0.0006 | 0.0012 | 0.013 | 0.0006 |
| Helianthus Annuus (sunflower) Seed Oil |  |  | 0.0001 |  |  |
| Total | 100 | 100 | 100 | 100 | 100 |

Example 2

The Addition of Benzyl Alcohol and Phosphoric Acid Promotes Preservation

Results of the comparative testing on Formulas 4-7 are shown in Table 2, suggesting that the addition of 0.1% benzyl alcohol and, in the meantime, replacing citric acid with phosphoric acid provide for a passing score in the AETs 1 using *Burkholderia* in the presence of three different flavors singly, peppermint, spearmint or wintergreen.

TABLE 4

| Formula No. | CPC (%) | NaF (%) | MIT (ppm) | Potassium Sorbate/Sodium Benzoate/Benzyl Alcohol (%

TABLE 4-continued

| Formula No. | CPC (%) | NaF (%) | MIT (ppm) | Potassium Sorbate/Sodium Benzoate/ Benzyl Alcohol (%) | Flavors | Acids | pH | Meets acceptance criteria/Does not meet acceptance criteria |
|---|---|---|---|---|---|---|---|---|
| Formula 5 | 0.075 | 0 | 0 | 0.1/0/0 | Wintergreen | Citric | 4.2 | Not meet |
| Formula 6 | 0.075 | 0 | 0 | 0.1/0.1/0 | Peppermint | Citric | 4.5 | Not meet |
| Formula 6 | 0.075 | 0 | 0 | 0.1/0.1/0 | Spearmint | Citric | 4.5 | Not meet |
| Formula 6 | 0.075 | 0 | 0 | 0.1/0.1/0 | Wintergreen | Citric | 4.5 | Not meet |
| Formula 7 | 0.075 | 0 | 0 | 0.1/0.1/0.1 | Peppermint | Phosphoric | 4.5 | Meet |
| Formula 7 | 0.075 | 0 | 0 | 0.1/0.1/0.1 | Spearmint | Phosphoric | 4.5 | Meet |
| Formula 7 | 0.075 | 0 | 0 | 0.1/0.1/0.1 | Wintergreen | Phosphoric | 4.5 | Meet |

Formulas 7 are prepared with the following ingredients, weight percentages given with respect to the final dual phase formulation:

TABLE 5

| Ingredients | Formula 7 Peppermint | Formula 7 Spearmint | Formula 7 Wintergreen |
|---|---|---|---|
| Water | Balance | Balance | Balance |
| Mineral Oil - Heavy | 12.46 | 12.45 | 12.35 |
| Glycerin | 10.00 | 10.00 | 10.00 |
| Sorbitol | 10.00 | 10.00 | 10.00 |
| Peppermint Flavor | 0.54 | | |
| Spearmint Flavor | | 0.54 | |
| Wintergreen Flavor | | | 0.64 |
| Sodium Saccharin | 0.050 | 0.05 | 0.05 |
| Sucralose | 0.01 | 0.01 | 0.01 |
| CPC | 0.075 | 0.075 | 0.075 |
| Potassium Sorbate | 0.10 | 0.10 | 0.10 |
| Sodium Benzoate | 0.10 | 0.10 | 0.10 |
| Benzyl Alcohol | 0.10 | 0.10 | 0.10 |
| Phosphoric Acid (85%) | 0.08 | 0.08 | 0.08 |
| Silicone Antifoam | 0.005 | 0.005 | 0.005 |
| Color agents | 0.0006 | 0.0006 | 0.0006 |
| Total | 100 | 100 | 100 |

Example 3

Multivalent Anions' Impact on the Availability of CPC Monomers

CPC is present in the aqueous phase as both micelles and CPC monomers. It is in the monomeric state that CPC is more effective as a preservative. Sizes of multivalent anions impact the formation of CPC micelles and CPC monomers. Bigger multivalent anions, like citrate, can push more CPC into micellar forms and therefore, lock CPC into rigid conformations in micellar forms. Smaller monovalent anions, e.g., $H_2PO_4^-$ or $Cl^-$, favor more dynamic and flexible CPC micelles, solutions of CPC with monovalent anions also have relatively higher molar percentage of CPC in monomeric forms.

The above impact is substantiated by surface tension measurements. Direct CPC monomer concentrations in both a citric buffer and a phosphoric buffer are determined by a surface tension measurement over a range of CPC concentrations. It is well established that surface tension decreases with increasing CPC monomer concentrations until CPC micelles start to form. A critical micelle concentration (CMC) is determined from such measurements, and lower CMC means less monomers existing in a solution. The CMC of CPC in a citric buffer is 30 ppm while the CMC in a phosphoric buffer is 40 ppm, determined from surface tension measurements.

Diffusion NMR and dynamic light scattering (DLS) were used to characterize the concentration of CPC monomers in CPC solutions, buffered with citric acid, phosphoric acid, and HCl, at condition similar to mouthwash (pH=4.5 and concentration at 0.075 wt %). The observed diffusion coefficient of CPC ($D_{NMR}$) is the weighted average between diffusion coefficient of CPC monomer ($D_{monomer(NMR)}$) and CPC micelle ($D_{micelle(DLS)}$). The CPC monomer concentration $X_{monomer}$ can be calculated from equation I:

$$D_{NMR} = X_{monomer} * D_{monomer(NMR)} + (1 - X_{monomer}) * D_{micelle(DLS)} \quad (I)$$

Diffusion coefficient of CPC monomer ($D_{monomer(NMR)} = 3.96 \times 10^{-10}$ m$^2$/s) was measured using a sample that CPC concentration is 0.0015 wt %, which is below the critical micelle concentration of CPC (~0.004 wt %).

Table 6 shows that the actual micelle sizes do not vary significantly with different buffer systems, represented by their diffusion coefficients measured by Dynamic Light Scattering (DLS). However, the diffusion coefficient of CPC with citrate measured by NMR method is 25-35% slower than systems with monovalent ions, such as $H_2PO_4^-$ and $Cl^-$, due to different percentages of monomers in the solutions. The CPC monomer percentages can be calculated using the equation above, $H_2PO_4^-$ results in 14 molar % CPC monomer, while CPC solution with has a monomer level of 16.3 molar %. With citrate ions, CPC monomer concentration drops to 7.2 mol %.

Another indicator of micelle property is its spin-spin relaxation time $T_2$. Protons $T_2$ was calculated based on the following equation II:

$$T_2 = 1(\pi v_{1/2}) \quad (II)$$

where $v_{1/2}$ is the peak width at half height. The $T_2$ value of the CPC aromatic protons in the solution buffered by citric acid is significantly lower, indicating that CPC micellar structure is more rigid with multivalent ions (citrate) than its counterparts with monovalent ions ($H_2PO_4^-$ and $Cl^-$), therefore, resulting lower bioavailability.

TABLE 6

| | DLS $D_{micelle(DLS)}$ (m$^2$/s) | Diffusion NMR $D_{NMR}$ (m$^2$/s) | $X_{monomer}$ (mol %) | $T_2$ (ms) |
|---|---|---|---|---|
| CPC + HCl | $6.62 \times 10^{-11}$ | $1.20 \times 10^{-10}$ | 16.3 | 66.0 |
| CPC + $H_3PO_4$ | $6.39 \times 10^{-11}$ | $1.11 \times 10^{-10}$ | 14.0 | 63.3 |
| CPC + citric acid | $6.38 \times 10^{-11}$ | $8.86 \times 10^{-11}$ | 7.2 | 47.0 |

Example 4

Optimized Mouthwashes

Formula optimization is conducted using both AET 1 and AET 2 described above, and Control Formula and Formulas 8-13 are tested. Control Formula contains 0.1% sorbate, 0.1% benzoate, 0.1% benzyl alcohol, 10% glycerin, and 10% sorbitol, and is prepared with the following ingredients, weight percentages given with respect to the final dual phase formulation:

TABLE 7

| Ingredients of Control Formula | Amounts |
|---|---|
| Mineral Oil | 12.35 |
| Beta Carotene | 0.0002 |
| Wintergreen Flavor | 0.64 |
| Demineralized Water | Balance |
| Sucralose | 0.010 |
| Saccharin | 0.05 |
| Cetylpyridinium Chloride | 0.075 |
| Glycerin | 10.00 |
| Sorbitol | 10.00 |
| Potassium Sorbate | 0.10 |
| Sodium Benzoate | 0.10 |
| Benzyl Alcohol | 0.10 |
| FD&C Blue #1 | 0.0004 |
| Silicone Antifoam | 0.005 |
| Phosphoric Acid (85%) | 0.08 |
| Total | 100.00 |

Formulas 8-13 are prepared following the ingredients of Control Formula listed in Table 7 except for those variations listed in Table 8.

Control Formula passes the AET1 using a fresh sample, but fails AET2 using an aged sample, indicating while the formula has passed the AET 1 *Burkholderia* test, it is not robust enough to pass the AET2 without the additional more benzyl alcohol.

TABLE 8

| Formula No. | Ingredient Variations | AET1 Fresh samples Meets acceptance criteria/Does not meet acceptance criteria | AET2 Aged samples Meets acceptance criteria/Does not meet acceptance criteria |
|---|---|---|---|
| Control | | Meet | Does not Meet |
| Formula 8 | 0.3% benzyl alcohol | Meet | Meet |
| Formula 9 | 0.5% benzyl alcohol | Meet | Meet |
| Formula 10 | 3.5% 1,2-propane-diol | Meet | Meet |
| Formula 11 | 7% 1,2-propane-diol | Meet | Meet |
| Formula 12 | 3% 1,3-propanediol | Meet | Meet |
| Formula 13 | 5% 1,3-propanediol | Meet | Meet |

In accordance with the results of formula optimization shown above, a representative formulation of the invention is prepared with the following ingredients, weight percentages given with respect to the final dual phase formulation:

TABLE 9

| Ingredients of Formula 8 | Phase A (hydrophobic) | Phase B (hydrophilic) |
|---|---|---|
| Mineral oil | 12.35 | — |
| Beta Carotene | 0.0002 | — |
| Sweet Wintergreen Mint Flavor | 0.6 | — |
| Menthol | 0.02 | — |
| Optacool | 0.025 | — |
| Sucralose | — | 0.01 |
| Sodium Saccharin | — | 0.05 |
| Phosphoric Acid - USP EP 85% | — | 0.08 |
| Hydrotrope | — | 10 |
| Humectant | — | 10 |
| FD&C Blue 1# | — | 0.0004 |
| Potassium Sorbate | — | 0.1 |
| Sodium Benzoate | — | 0.1 |
| Benzyl Alcohol | — | 0.5 |
| CPC | — | 0.075 |
| Antifoam agent | — | 0.005 |
| Water | — | Balance |

While the present invention has been described with reference to embodiments, it will be understood by those skilled in the art that various modifications and variations may be made therein without departing from the scope of the present invention as defined by the appended claims.

What is claimed is:

1. A dual phase mouthwash comprising a hydrophilic phase; a hydrophobic phase; a hydrotrope; an effective amount of a preservative comprising the combination of potassium sorbate, sodium benzoate, and benzyl alcohol; cetyl pyridinium chloride (CPC); and an acid selected from hydrochloric acid, phosphoric acid, and combinations thereof, wherein the preservatives are present in amounts by weight of the mouthwash: potassium sorbate 0.01-0.5%; sodium benzoate 0.01-0.5%; benzyl alcohol 0.01-1%.

2. The mouthwash of claim 1 wherein the acid is phosphoric acid.

3. The mouthwash of claim 1 wherein the hydrotrope component comprises glycerin, propylene glycol, and/or 1,3 propanediol.

4. The mouthwash of claim 1 wherein the hydrotrope component comprises glycerin.

5. The mouthwash of claim 4 wherein the hydrotrope component comprises 1-40% glycerin by weight of the mouthwash.

6. The mouthwash of claim 1 wherein the hydrophobic phase comprises an oil selected from isopropyl myristate, mineral oil, an edible oil, and combinations thereof.

7. The mouthwash of claim 1 wherein the hydrophilic phase comprises the hydrotrope component.

8. The mouthwash of claim 1 comprising 0.07-0.3% potassium sorbate, 0.08-0.3% sodium benzoate, and benzyl alcohol 0.08-0.8%, by weight of the mouthwash.

9. The mouthwash of claim 1 comprising 0.001-1% CPC by weight of the mouthwash.

10. The mouthwash of claim 1 further comprising one or more of flavors selected from spearmint, peppermint, wintergreen, sassafras, clove, sage, eucalyptus, marjoram, cinnamon, lemon, lime, grapefruit, orange, menthol, carvone, anethole, and a combination thereof.

11. The mouthwash of claim 10 further comprising one or more of flavors selected from spearmint, peppermint, wintergreen, menthol, and a combination thereof.

12. The mouthwash of claim 1 comprises 0.01-2% one or more of flavors by weight of the mouthwash.

13. The mouthwash of claim 1 further comprising one or more of humectants.

14. The mouthwash of claim 13 wherein the humectant is sorbitol.

15. The mouthwash of claim 14 wherein the sorbitol is present in an amount of 1-30% by weight of the mouthwash.

16. A dual phase mouthwash comprising a hydrophilic phase, a hydrophobic phase, a hydrotrope, about 0.1% potassium sorbate by weight of the mouthwash, about 0.1% sodium benzoate by weight of the mouthwash, and about 0.5% benzyl alcohol by weight of the mouthwash, CPC, one or more flavors, and phosphoric acid.

17. A method to improve oral health comprising applying an effective amount of the mouthwash of claim 1 to the oral cavity of a subject in need thereof to
   a. reduce or inhibit formation of dental caries,
   b. reduce, repair or inhibit early enamel lesions,
   c. reduce or inhibit demineralization and promote remineralization of the teeth,
   d. reduce hypersensitivity of the teeth,
   e. reduce or inhibit gingivitis,
   f. promote healing of sores or cuts in the mouth,
   g. inhibit microbial biofilm formation in the oral cavity,
   h. raise and/or maintain plaque pH at levels of at least pH 5.5 following sugar challenge,
   i. reduce plaque accumulation,
   j. treat, relieve or reduce dry mouth,
   k. whiten teeth,
   l. enhance systemic health, including cardiovascular health,
   m. reduce erosion of the teeth,
   n. to immunize the teeth against cariogenic bacteria and their effects, and/or
   o. clean the teeth and oral cavity.

* * * * *

UNITED STATES PATENT AND TRADEMARK OFFICE
CERTIFICATE OF CORRECTION

PATENT NO. : 10,588,835 B2
APPLICATION NO. : 15/848072
DATED : March 17, 2020
INVENTOR(S) : Jeffrey Merl Miller et al.

It is certified that error appears in the above-identified patent and that said Letters Patent is hereby corrected as shown below:

On the Title Page

Item (56), under "OTHER PUBLICATIONS", Line 11, delete "Plague" and insert -- Plaque --, therefor.

Item (56), under "OTHER PUBLICATIONS", Line 13, delete "Plague" and insert -- Plaque --, therefor.

In the Specification

In Column 10, Line 54, delete "FMB" and insert -- HLB --, therefor.

In Column 12, Line 30, delete "Humecants" and insert -- Humectants --, therefor.

In Column 14, Line 19, delete "<51." and insert -- <51>. --, therefor.

In Column 14, Line 19, delete "testis" and insert -- test is --, therefor.

In Column 18, Line 43, after "CPC solution with", insert -- Cl⁻ --, therefor.

Signed and Sealed this
Thirtieth Day of June, 2020

Andrei Iancu
*Director of the United States Patent and Trademark Office*